(12) United States Patent
Bhagyalakshmi et al.

(10) Patent No.: US 6,706,077 B2
(45) Date of Patent: Mar. 16, 2004

(54) HAIR COLORING COMPOSITIONS

(75) Inventors: Krithivasan Bhagyalakshmi, Karnataka (IN); Indu Mani, Karnataka (IN); Govindarajan Raman, Maharashtra (NL)

(73) Assignee: Unilever Home & Personal Care USA, division of Conopco, Inc., Chicago, IL (US)

( * ) Notice: Subject to any disclaimer, the term of this patent is extended or adjusted under 35 U.S.C. 154(b) by 30 days.

(21) Appl. No.: 10/091,151

(22) Filed: Mar. 5, 2002

(65) Prior Publication Data

US 2002/0166182 A1 Nov. 14, 2002

(30) Foreign Application Priority Data

Mar. 7, 2001 (IN) ........................................ 229/MUM/01
Apr. 18, 2001 (GB) .............................................. 0109533

(51) Int. Cl.$^7$ ................................................. A61K 7/13
(52) U.S. Cl. ....................... 8/405; 8/406; 8/426; 8/428; 8/431; 8/546; 8/637.1
(58) Field of Search ........................... 8/405, 406, 424, 8/428, 431, 546, 637.1

(56) References Cited

U.S. PATENT DOCUMENTS 3,941,835 A      3/1976  Riccardi ..................... 260/519
3,993,436 A  *  11/1976  Fujinuma ..................... 8/10.2
4,566,875 A      1/1986  Grollier et al. ................. 8/408

OTHER PUBLICATIONS

Search Report under Section 17, Application No. GB 0109533.0 dated Oct. 15, 2001.
International Search Report Application No. PCT/EP 02/02344 mailed Aug. 8, 2002.
Patent Abstract of Japan, vol. 018, No. 371 (C–1224) & JP 06 100423 A (Takeo Kaneko).

* cited by examiner

Primary Examiner—Yogendra N. Gupta
Assistant Examiner—Eisa B Elhilo
(74) Attorney, Agent, or Firm—Milton L. Honig

(57) ABSTRACT

A coloring system for hair and/or skin comprises at least three separately packaged components:
  a) a thio compound capable of breaking the S—S bond between cysteine residues, and an alkaline reagent;
  b) a material and/or extract obtainable from the mucuna plant; and
  c) an oxidizing agent.

Figure 1A:
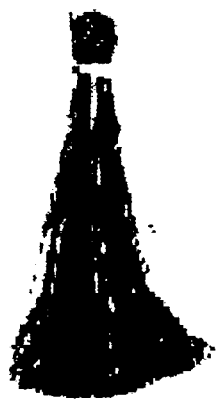

28 Claims, 1 Drawing Sheet

HAIR COLORING COMPOSITIONS

TECHNICAL FIELD

The present invention relates to compositions for changing the colour of keratinic fibers especially human hair. The composition can also be used to darken human skin.

BACKGROUND

Melanin is a naturally occurring pigment present in hair and skin and it is synthesised in melanocytes in the presence of the enzyme tyrosinase. Two different melanins are found in human hair, eumelanin and pheomelanin. While brown and black hair contain eumelanin, pheomelanin is found in red hair.

The enzyme tyrosinase catalyses the hydroxylation of tyrosine to 3,4-dihydroxyphenylalanine (DOPA) and its subsequent oxidation to dopachrome. Dopachrome further undergoes a series of complex reactions to form eumelanins and pheomelanins (often collectively termed melanin).

Efforts have been made in the past to provide a hair dyeing process that mirrors the formation of the hairs' natural pigment, melanin. These efforts relied in general upon treatment of hair with a recognized intermediate of the melanin pathway, most often tyrosine or DOPA or its analogs resulting in formation of melanin and consequent colouring of hair. An oxidative post-treatment is usually required to get satisfactory, fast colours.

DOPA is available naturally in nature. It can also be prepared synthetically and many hair compositions use the synthetic form that is available commercially. However, there have been some problems associated with the use of synthetic DOPA. Synthetic DOPA is reported to be unstable and to have a tendency to oxidise prematurely. Moreover, it can also be costly to synthesise. Further, there is a consumer preference for natural products as these are perceived to be safe.

An example of a natural source of DOPA is Mucuna, a genus belonging to the family Leguminosae with about 15 species, some of which can be found in India. Annual or perennial twining herbs or shrubs distributed in the tropics and subtropics, Mucuna includes many species like *Mucuna urens, Mucuna puriens* and *Mucuna sloanei*.

While providing for a stable, natural form of DOPA to darken skin or hair is highly desirable, colour substantivity to the keratinic fibre and colour fastness is often difficult to achieve with natural materials.

PRIOR ART

Brown et al, J of Soc, of Cos. Chemists, 48, 1997, 133 relates to a process of converting DOPA on hair to 5,6-dihydroxyindole by careful selection of the oxidant. This indole is a precursor of black eumelanin and it is readily polymerised in situ to dye the hair black. Nucleophiles such as cysteine and other throls are added to produce a wide range of shades on hair.

U.S. Pat. No. 3,993,436 discloses a three component hair colouring system comprising of a cutting agent (for the cysteine bond in hair), tyrosine and/or synthetic DOPA or its derivatives and an oxidising agent. The cutting agent helps in better dyeing by making hair more susceptible to the uptake of organic molecules, like dyes.

EP0914816 discloses extracts from several plant sources, including Mykania Glomerata, Japanese pepper and Parameria laevigata that have superior tyrosinase promoting actions and prevent grey hair formation or darken grey hair.

U.S. Pat. No. 3,941,835 discloses the recovery of L-Dopa from several naturally occurring materials, including the seeds of *Mucuna puriens*.

The prior art is therefore mainly concerned with the use of synthetic DOPA and its analogs or precursors for colouring skin and hair. As already mentioned, there may be problems associated with the use of synthetic DOPA. Natural materials that promote tyrosinase activity are known in the art, however these may not give as good a colouring as systems using DOPA.

The prior art does not therefore disclose a stable, natural source of DOPA to colour hair and skin. Also the prior art does not indicate how to achieve superior colouring and colour fastness using a natural product.

The applicants have now found that it is possible to obtain superior dark colour on hair and skin using a colouring system comprising the Mucuna plant or its extract, a cysteine cutting agent and an oxidising agent. The colour generated by this process is superior to the one generated using synthetic DOPA and it is possible to generate a wide range of shades by this process. Mucuna being cheap and readily available, the invention also provides for an inexpensive process to colour skin and/or hair. The product will be safe as the composition is based on a natural material.

SUMMARY OF THE INVENTION

Thus the present invention provides for a system for colouring hair and/or skin comprising at least three separately packaged components: a) a thio compound capable of cutting the cysteine bond and an alkaline reagent which may or may not be separately packaged b) Mucuna and c) an oxidising agent. The colouring system may be suitably supplied in the form of a combination kit. A method of dyeing skin and/or hair is also provided comprising the sequential steps of application of the thio compound and alkaline reagent followed by the application of Mucuna and finally applying the oxidising agent.

The term mucuna encompasses materials and extracts obtainable from the mucuna plant, including the dried powder of the plant or parts of the plant, the extract obtained by solvent extraction of mucuna or a wet homogenate in a suitable solvent. The term also encompasses solutions, dispersions and suspensions of the same.

The colouring system of the invention is based on a natural material, provides for a wide range of shades and is inexpensive and safe.

DEFINITION OF THE INVENTION

According to one aspect of the invention there is provided a colouring system for hair and/or skin comprising at least three separately packaged components:

a) a thio compound capable of breaking the S—S bond between cysteine residues, and an alkaline reagent;

b) a material and/or extract obtainable from the mucuna plant; and c) an oxidising agent.

According to a preferred aspect of the invention there is provided a colouring system for hair and/or skin comprising at least three separately packaged components:

a. a thio compound capable of cutting the S—S cysteine bond, preferably in the form of a fluid composition having a concentration of from 0.01 to 8% weight/ volume and an alkaline reagent, said alkaline reagent being supplied with the thio compound or as a separate package.

b. Mucuna or its extract, preferably in the form of a fluid composition having a concentration of from 0.1 to 99% weight/volume c. an oxidising agent, preferably in the form of a fluid composition having a concentration of from 0.01 to 1% weight/volume.

According to another aspect of the invention, there is provided a method for sequential treatment of the hair and/or skin by the colouring system according to the invention, comprising the specific sequence of:

treating hair and/or skin with a thio compound capable of breaking the S—S bond between cysteine residues, in the form of an aqueous solution; applying to the hair and/or skin mucuna and/or an extract thereof; and treating the hair and/or skin with an aqueous solution of an oxidising agent.

In a preferred embodiment, the method comprises the specific sequence of a. treating hair and/or skin with a thio compound capable of cutting the cysteine S—S bond in the form of a fluid composition having a concentration of from 0.01 to 8% weight/volume and an alkaline reagent.

b. applying to the hair and/or skin mucuna and/or its extract in the form of a fluid composition having a concentration of from 0.1 to 99% weight/volume and c. treating the hair and/or skin with a fluid composition of an oxidising agent having a concentration of from 0.01 to 5% weight/volume.

In a preferred aspect of the invention, the colouring system of the invention is provided as a combination kit comprising the three components mentioned above, said combination kit also having an instruction manual containing instructions for sequential use of the ingredients on hair and/or skin.

DETAILED DESCRIPTION OF THE INVENTION

All parts herein are by weight unless otherwise specified.

The present invention relates to a colouring system suitable for hair and/or skin comprising at least three separately packaged components. The three components are a thio compound capable of cutting the S—S bond of cysteine and an alkaline reagent present with the thio compound or present as a separately packaged alkaline reagent, Mucuna and/or its extract and an oxidising agent.

The colouring system of the invention can be suitably supplied in the form of a combination kit.

Thio Compound

Thio compounds or the cutting agents useful for the invention include mercaptans, thioglycolic acid, dithiothreitol (DTT), dithioerythritol (DTE), sodium sulphite, sodium metabisulphite or mixtures thereof. The cutting agent is known to break (or cleave) the S—S bond between the cysteine residues of hair and the hair readily takes up organic molecules, as maybe present in mucuna, after this process. The terms cut, break, cleave and related terms used herein are employed synonymously.

DTT and DTE are preferred thio compounds. DTT is especially preferred.

The thio compound is preferably used in an amount from 0.01 to 8% by weight of a fluid composition, more preferably from 0.1 to 5% by weight and most preferably from 0.1 to 2% by weight of a fluid composition.

Examples of suitable compositions include solutions, gels, creams, sprays and lotions.

The thio compound should be used with an alkaline reagent. It is preferably buffered to a pH of at least 7.5 using an alkaline reagent when water is used as a fluid. However, the thio compound and the alkaline reagent may be supplied separately. Examples of alkaline reagents suitable for the invention include ammonia, potassium hydroxide, sodium hydroxide, polyethyleneimine (PEI) or mixtures thereof. When used separately, the alkaline reagent is preferably used in an amount from 0.01 to 5% by weight of an aqueous solution.

Mucuna

Any species of mucuna may be used for the colouring system of the invention. Examples of mucuna species include *Mucuna urens, Mucuna puriens, Mucuna sloanei, Mucuna birdwoodiana* and *Mucuna gigantea*. Especially preferred is *mucuna pruriens* (also known as velvet bean).

The leaves, stem, seeds, flowers and/or fruits of the plant can be used for the purposes of the invention. Especially preferred are the seeds and leaves.

Parts of the plant as given above can be suitably dried and powdered and supplied. When applied to the hair, a suitable form of application would be to make an aqueous dispersion of the powdered material.

It is also possible to supply mucuna in the form of an extract. The extract of the raw and dried material can be obtained by methods generally known to obtain an extract from a plant.

Suitable solvents for extraction include water (cold (eg, 0 to 30° C.) or hot (eg, 30 to 100° C.)), acids in the pH range 2–7, alkaline materials in the pH range 7–8.5 and alcohols. Alcohols suitable for the invention include methanol and ethanol.

Acids and alkalis are preferably used as solutions of concentration from 0.001 to 20%. Buffers in the specified pH range may also be used.

It is preferable to use acids in the pH range from 2 to 5. An especially preferred acid is acetic acid, which can be suitably used in a concentration from 0.001 to 20% weight/volume, more preferably from 0.01 to 10% and most preferably from 0.1 to 2%.

It is not essential to remove the solvent used for extraction. However, it is possible to completely remove the solvent by conventional methods used in the art and use the concentrated extract so obtained, especially when an alcohol is used for extraction.

When applied to the hair and/or skin Mucuna can be suitably used as a fluid composition. It is used in a concentration range from 0.1 to 99% weight/volume, more preferably from 2 to 90% and most preferably from 10 to 90%.

Water is an especially preferred fluid. Mucuna can be used as a solution, dispersion or suspension and examples of suitable compositions include creams, solutions, lotions, gels and sprays.

Optionally, other natural colouring agents and/or synthetic DOPA may also be added provided the total amount is not greater than 40% by weight with respect to mucuna. Examples of natural colouring agents are henna, green tea, areca nut, raw tamarind, gooseberry and the extracts of these materials amongst others.

Optionally, the mucuna may be supplied in a suitable vehicle. Vehicles conventionally known in the art, examples of which include stearic acid, stearyl alcohol, glyceryl monostearate, oleyl alcohol, dimethyl polysiloxane, petroleum, mineral oil, corn oil, lanolin, sesame seed oil, isopropyl palmitate, isopropyl stearate and coconut oil are suitable for the invention.

Other ingredients like thickeners, humectants, perfumes, stabilisiers and preservatives may also be added to mucuna.

Oxidising Agent

The oxidising agent is preferably chosen from a persulfate or ferric chloride. Examples of persulphates are ammonium persulphate and potassium persulphate. Ferric chloride is especially preferred. The oxidising agent is used in an amount of 0.01 to 1% by weight of a fluid composition, preferably from 0.05 to 0.2% and more preferably from 0.1–0.2% by weight of a fluid composition. Water is a preferred fluid. The oxidising agent can be suitably used in the form of a solution, gel, cream, spray or lotion.

Method of Application on Skin/Hair

The present invention also relates to a method of colouring hair and/or skin by a sequential treatment with the three component system that has been described. By sequential treatment is meant that the components are applied one after the other in the specific sequence described below. It is preferred that the three component system is present as a kit with clear instructions on the application of the kit components.

The thio compound is applied first to the hair/skin as a fluid composition along with an alkaline reagent. The amount of the thio compound in the solution is from 0.01 to 8% weight/volume and that of the alkaline reagent used is from 0.01 to 5% weight/volume. A minimum of 5 minutes is required for a single application.

In the second step, mucuna is applied to the hair/skin. Mucuna is applied as a fluid composition of concentration from 0.1 to 99% by weight of mucuna. A suitable solvent is acetic acid of concentration from 0.01 to 20% by weight. Other optional ingredients maybe present in the composition. The solution is applied for a period of at least 5 minutes.

In the third step, the oxidising agent is applied to the hair/skin as a fluid composition of concentration from 0.01 to 5% by weight for a period of at least five minutes.

It is preferable but not essential that the hair/skin be rinsed with water at the end of each step.

It is preferable that each component is applied once, though repeated application is possible.

While a single application of the three components is sufficient for colouring, in a preferred embodiment, the entire process is repeated five times.

The hair/skin colouring achieved by the present method is permanent in nature. By permanent is meant that the colour will not be removed by water or conventional surfactants.

The above method of darkening skin/hair can achieve a variety of shades.

THE KIT

The kit used in the present invention is a container selected from paper, wood and/or plastic packaging or metal plastic strips in which the individual ingredients, the thio compound, mucuna and the oxidising agent are packed separately. The alkaline reagent may be present with the thio compound or optionally may be provided as a separate package. The instruction is in the form of printed information printed on the packaging or on the strip or pouch containing the ingredients. The instructions are in national or any local or regional language.

In one example of the kit, the container of the kit is a paper box having three compartments of varying sizes. The cutting agent, mucuna and the oxidising agent are provided in three separate enclosures of varying size and are present as solutions/dispersions.

Optionally, an applicator for supplying the solution may also be present in the kit. A pair of gloves suitable for use when applying the solutions may also be provided with the kit.

The invention is further illustrated by the following non-limiting examples, in which parts and percentages are by weight unless otherwise specified.

Reference is made in the Examples to FIG. 1 of the accompanying drawings.

EXAMPLES

Extraction of Mucuna

Fresh leaves of mucuna were dried in an oven at 80° C. to a moisture content of <1%. The dried leaves were then ground finely and extracted with a 1% solution of acetic acid. This solution in acetic acid is used for further tests.

Comparative Example A and B and Example 1

Three white hair swatches (each swatch being 3–5 cms long with 100–200 hair strands) were prepared and washed with a commercially available shampoo. One swatch was used as a control (Comparative Example A) and was not treated further. The other two were used for testing the colouring systems of the invention and outside the invention.

Step 1

The hair swatches of Comparative Example B and Example 1 were treated with a solution of 0.2% DTT in an aqueous solution of 0.5% PEI for 5 minutes. The hairs were then dried.

Step 2

The hair swatch of Comparative Example B was subsequently treated with a 4 mM solution of DL-DOPA (ex ICN Pharmaceuticals Ltd. U.S.A.) and 25 Units of mushroom tyrosinase/ml of solution (ex Sigma Chemical Co. U.S.A.) for 5 minutes and then dried.

The hair swatch of Example 1 was treated for 5 minutes with the solution of the mucuna extract prepared above and then dried.

Step 3

The hair swatches of Comparative Example B and Example 1 were then dipped in an aqueous solution of $FeCl_3$ (0.16%) for 5 minutes and then air dried for 15 minutes.

Steps 1 to 3 were repeated five times for Comparative Example B and Example 1.

Hair swatches were then left to dry overnight and washed with a shampoo next day.

Determination of Hair Colour

The colour of the hair swatches was determined on a Sigma Scan Pro and is measured as grey scale values. Hair colour was determined on a scale of 0 to 255, wherein 0 is black and 255 is white.

The data are presented in Table 1

TABLE 1

| Example | Grey scale value |
|---------|------------------|
| A | 211.7 |
| B | 119.5 |
| 1 | 76.4 |

The data in Table 1 shows that the colouring system of the invention is superior to a colouring system using synthetic DOPA.

Comparative Example C, Example 2 and 3

Three hair swatches containing a mixture of white and black hair (each being 3–5 cms long with 100–200 hair strands) were washed with a commercially available shampoo. One swatch was used a control (Comparative Example C) and did not undergo further treatment.

Step 1

The hair swatch of Example 2 was then treated with a solution of 0.2% DTT in an aqueous solution of 0.05 N KOH for 5 minutes. The hair swatch of Example 3 was treated with a soluton of 0.2% DTT in an aqueous solution of 0.5% PEI for 5 minutes. The hairs were then dried.

Step 2

The hair swatches of Examples 2 and 3 were subsequently treated with the solution of the mucuna extract prepared above, for 5 minutes and then dried.

Step 3

The hair swatches of Example 2 and 3 were then dipped in an aqueous solution of $FeCl_3$ (0.16%) for 5 minutes and then air dried for 15 minutes.

Steps 1–3 were repeated five times for Examples 2 and 3.

Hair swatches were then left to dry overnight and washed with a shampoo next day.

Determination of Hair Colour

The colour of the hair swatches was determined on a Sigma Scan Pro and measured as grey scale value. Hair colour was determined on a scale of 0 to 255, wherein 0 is black and 255 is white.

The data are presented in Table 2.

TABLE 2

| Example | Grey scale value |
|---------|------------------|
| C | 132.5 |
| 2 | 95.8 |
| 3 | 76.3 |

Table 2 shows that the colouring system of the invention shows good dyeing even when different alkaline systems are used.

Figure 1B:
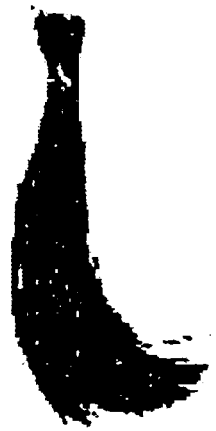
Figure 1C:

A visual representation of the results is provided in FIG. 1. FIGS. 1a, 1b and 1c refer to Comparative Example C, Example 2 and Example 3 respectively.

Thus the present invention provides for a novel, stable and inexpensive colouring system comprising the Mucuna plant or its extract, a cysteine cutting agent and an oxidising agent. The colour generated by this process is superior to the one generated using synthetic DOPA and it is possible to generate a wide range of shades by this process. The product will be safe as the composition is based on a natural material.

What is claimed is:

1. A colouring system for hair and/or skin comprising at least three separately packaged components:
   a) a thio compound capable of breaking the S—S bond between cysteine residues, and an alkaline reagent;
   b) a material and/or extract obtainable from the mucuna plant; and
   c) an oxidising agent.

2. The colouring system of claim 1 wherein the thio compound is selected from mercaptans, thioglycolic acid, dithiothreitol, dithioerythritol, sodium sulphite, sodium metabisulphite and mixtures thereof.

3. The colouring system of claim 2 wherein the thio compound is selected from dithiothreitol and dithioerythritol.

4. The colouring system of claim 1 wherein the thio compound is a separately packaged solution of concentration from 0.1 to 5% by wt.

5. The colouring system of claim 4 wherein the thio compound is a separately packaged aqueous solution of concentration from 0.1 to 2% by wt.

6. The colouring system of claim 1 wherein the alkaline reagent is selected from ammonia, potassium hydroxide, sodium hydroxide, polyethyleneimine and mixtures thereof.

7. The colouring system of claim 1 wherein the alkaline reagent is supplied as a separately packaged solution of concentration from 0.01 to 5% by wt.

8. The colouring system of claim 1 wherein the material and/or extract is a separately packaged solution of concentration from 1 to 90% by wt.

9. The colouring system of claim 8 wherein the material and/or extract is a separately packaged solution of concentration from 20 to 90% by wt.

10. The colouring system of claim 1 wherein the material and/or extract is selected from *mucuna urens, mucuna sloanei, mucuna birdwoodonia, mucuna giagantea* and *mucuna puriens*.

11. The colouring system of claim 10 wherein the material and/or extract is from the species *mucuna puriens*.

12. The colouring system of claim 1 wherein the material and/or extract is the raw or dried leaf, root, stem, flower and/or seed of the species mucuna.

13. The colouring system of claim 12 where the material and/or extract is the seeds and/or leaves of the species mucuna.

14. The colouring system of claim 1 wherein the material and/or extract is an extract obtained using a suitable solvent.

15. The colouring system of claim 14 wherein the extract is obtainable by extracting mucuna using solvents selected from hot water, cold water, acids in the pH range 2–7, alcohols and alkaline materials in the pH range 7–8.5.

16. The colouring system of claim 15 wherein the material and/or extract is obtainable using acids in the pH range from 2–5.

17. The colouring system of claim 16 wherein the acid is used in a concentration from 0.001 to 20%.

18. The colouring system of claim 17 wherein the acid is used in a concentration from 0.01 to 10%.

19. The colouring system of claim 18 wherein the acid is used in a concentration from 0.1 to 2%.

20. The colouring system of claim 15 wherein the acid is acetic acid.

21. The colouring system of claim 1 wherein not more than 40 wt % of other colouring agents, preferably selected from henna, areca nut, raw tamarind, gooseberry and/or synthetic DOPA, are present along with the material and/or extract.

22. The colouring system of claim 1 wherein the material and/or extract is present in a suitable vehicle, preferably selected from stearic acid, stearyl alcohol, glyceryl monostearate, oleyl alcohol, dimethyl polysiloxane, petroleum, mineral oil, corn oil, lanolin, sesame seed oil, isopropyl palmitate, isopropyl stearate and coconut oil.

23. The colouring system of claim 1 further comprising one or more ingredients selected from thickeners, humectants, perfumes, stabilisers and preservatives.

24. The colouring system of claim 1 wherein the oxidising agent is present as a solution of concentration from 0.05 to 0.2%.

25. The colouring system of claim 24 wherein the oxidising agent is present as a solution of concentration from 0.1% to 0.2%.

26. The colouring system of claim 1 wherein the oxidising agent is selected from ferric chloride, persulphates and mixtures thereof.

27. The colouring system of claim 26 wherein the oxidising agent is ferric chloride.

28. A method for sequential treatment of the hair and/or skin by the colouring system according to claim 1, comprising the specific sequence of:

treating hair and/or skin with a thio compound capable of breaking the S—S bond between cysteine residues, in the form of an aqueous solution; applying to the hair and/or skin mucuna and/or an extract thereof; and treating the hair and/or skin with an aqueous solution of an oxidising agent.

* * * * *